(12) United States Patent
Yang et al.

(10) Patent No.: US 10,383,632 B2
(45) Date of Patent: Aug. 20, 2019

(54) BENDING CONTROL MECHANISM AND SURGICAL INSTRUMENT WITH SAME

(71) Applicants: SHANGHAI YISI MEDICAL TECHNOLOGY CO., LTD., Shanghai (CN); YISI(SUZHOU)MEDICAL TECHNOLOGY CO., LTD., Suzhou, Jiangsu (CN)

(72) Inventors: Guang Yang, Shanghai (CN); Honglin Nie, Shanghai (CN); Anhua Li, Shanghai (CN); Xiliang Zhang, Shanghai (CN); Xiufeng Shi, Shanghai (CN)

(73) Assignees: SHANGHAI YISI MEDICAL TECHNOLOGY CO., LTD., Shanghai (CN); YISI (SUZHOU) MEDICAL TECHNOLOGY CO., LTD., Suzhou, Jiangsu (CN)

( * ) Notice: Subject to any disclaimer, the term of this patent is extended or adjusted under 35 U.S.C. 154(b) by 387 days.

(21) Appl. No.: 15/324,266

(22) PCT Filed: Sep. 22, 2015

(86) PCT No.: PCT/CN2015/090208
§ 371 (c)(1),
(2) Date: Jan. 6, 2017

(87) PCT Pub. No.: WO2016/115918
PCT Pub. Date: Jul. 28, 2016

(65) Prior Publication Data
US 2017/0196559 A1    Jul. 13, 2017

(30) Foreign Application Priority Data
Jan. 19, 2015   (CN) .......................... 2015 1 0026528

(51) Int. Cl.
*A61B 17/072* (2006.01)
*A61B 17/068* (2006.01)
(Continued)

(52) U.S. Cl.
CPC .. *A61B 17/07207* (2013.01); *A61B 17/00234* (2013.01); *A61B 17/068* (2013.01);
(Continued)

(58) Field of Classification Search
CPC ................ A61B 17/068; A61B 17/072; A61B 17/07207; A61B 17/115; A61B 2017/07214; A61B 2017/2923; A61B 2017/2927; A61B 2017/2929; A61B 2017/2946
USPC .............. 227/19, 175.1, 176.1, 175.2, 180.1; 606/139, 153, 219
See application file for complete search history.

(56) References Cited

U.S. PATENT DOCUMENTS 5,704,534 A * 1/1998 Huitema .......... A61B 17/07207
                                                227/175.1
5,713,505 A * 2/1998 Huitema .......... A61B 17/07207
                                                227/175.1
(Continued)

*Primary Examiner* — Scott A Smith

(57) ABSTRACT

A bending control mechanism includes a turning power input mechanism A, a turning transmission mechanism B, a locking mechanism C and a linear power output mechanism D; further, the turning power input mechanism A and the turning transmission mechanism B which are coaxially arranged have a relative rotating angle range in the circumferential direction; the turning power input mechanism A sequentially rotates in an angle I, an angle range II and an angle III while rotating relative to the turning transmission mechanism B from one end angle to the other end angle within a relative rotating angle range, wherein the angle I or the angle III corresponds to turning; the angle range II corresponds to a locking state. With the adoption of the mechanism, the problem of turning and fixing of the surgical instrument in a human body during surgery is solved, and the risk of surgery is reduced.

18 Claims, 3 Drawing Sheets

(51) Int. Cl.
   *A61B 90/00*    (2016.01)
   *A61B 17/00*    (2006.01)
   *A61B 17/29*    (2006.01)

(52) U.S. Cl.
   CPC ............ *A61B 90/03* (2016.02); *A61B 17/072* (2013.01); *A61B 2017/00318* (2013.01); *A61B 2017/00407* (2013.01); *A61B 2017/07214* (2013.01); *A61B 2017/2923* (2013.01); *A61B 2017/2927* (2013.01); *A61B 2090/035* (2016.02); *A61B 2090/036* (2016.02)

(56) References Cited

U.S. PATENT DOCUMENTS

| | | | | |
|---|---|---|---|---|
| 5,823,066 | A  * | 10/1998 | Huitema | A61B 17/07207 74/527 |
| 7,624,902 | B2 * | 12/2009 | Marczyk | A61B 17/07207 227/175.1 |
| 7,648,055 | B2 * | 1/2010 | Marczyk | A61B 17/072 227/175.1 |
| 8,061,576 | B2 * | 11/2011 | Cappola | A61B 17/072 227/175.1 |
| 8,132,706 | B2 * | 3/2012 | Marczyk | A61B 17/07207 227/175.1 |
| 8,336,754 | B2 * | 12/2012 | Cappola | A61B 17/068 227/175.2 |
| 8,608,045 | B2 * | 12/2013 | Smith | A61B 17/07207 227/175.2 |
| 8,636,766 | B2 * | 1/2014 | Milliman | A61B 17/07207 606/219 |
| 8,789,741 | B2 * | 7/2014 | Baxter, III | A61B 17/07207 227/180.1 |

* cited by examiner

BENDING CONTROL MECHANISM AND SURGICAL INSTRUMENT WITH SAME

CROSS REFERENCE OF RELATED APPLICATION

This is a U.S. National Stage under 35 U.S.C. 371 of the International Application PCT/CN2015/090208, filed Sep. 22, 2015, which claims priority under 35 U.S.C. 119(a-d) to CN 201510026528.0, filed Jan. 19, 2015.

BACKGROUND OF THE PRESENT INVENTION

Field of Invention

The invention relates to a bending control mechanism for surgical stapler, and more particularly to a mechanism for controlling turning and locking the jaw of the endoscopic stapler.

Description of Related Arts

The action principle of surgical stapler is as follows: two corresponding jaws (commonly referred to as anvil assembly and cartridge assembly) are closed to clamp tissue; and then metal suturing nails in cartridge of the stapler are pushed out to perform molding, to sew tissue together. Some staplers are provided with a cutting knife, to cut off the sewn tissue together.

With the progress of technology, the traditional mode of operation is gradually turned into the endoscopic surgery. In the endoscopic surgery, a number of small incisions with diameter of 5-12 mm are made in different parts of the abdomen or chest; camera lens and a variety of special surgical instruments are inserted in these small incisions; images of various organs in the abdominal cavity taken by the camera inserted in the abdominal cavity are transmitted to the TV screen; by observing the images, the surgeon operates a variety of surgical instruments to complete the operation.

Wherein, the endoscopic stapler plays the most crucial role in the operation. Due to the limitation of space in the abdominal cavity or thoracic cavity, in some extreme cases, the traditional linear endoscopic stapler is unable to effectively reach the surgical site to perform clamping, transection and anastomosis of tissue; therefore, an elbow stapler with stapler jaw (including anvil assembly and cartridge assembly) capable of turning is required. In a straight line state, this kind of elbow stapler capable of turning enters the thoracic cavity or abdominal cavity through puncture outfit; the jaw is controlled by the bending control mechanism on the in-vitro handle to bend to a certain angle; and a series of operations such as clamping, transection and anastomosis are performed on the surgical site. After the operation is completed, the elbow stapler exits the body after turning to the straight line state.

Thus, there is an urgent need for a reasonable bending control mechanism, to control the angle required for rotation of the stapler jaw, so that the operation is convenient; at the same time, the angle required for the stapler jaw is firmly locked, to prevent security risks in the unpredictable force.

SUMMARY OF THE PRESENT INVENTION

In view of the defects in the prior art, an object of the present invention is to design a simple control mechanism, to reach the purpose of making the stapler jaw turn by pulling the wrench, and lock the stapler jaw at the selected angle. Thus, in the thoracic cavity or abdominal cavity, even the stapler jaw is subject to unpredictable forces, the jaw will not turn, thereby reducing the potential risks.

A bending control mechanism according to the present invention comprises: a wrench constituting a turning power input mechanism A and a lifting ring which synchronously rotates with the wrench; a central shaft constituting a turning transmission mechanism B; a cam lock, a compression spring and a housing constituting a locking mechanism C, wherein the cam lock is engaged with the turning transmission mechanism B; and a rack constituting a linear power output mechanism D, wherein the rack is engaged with a gear arranged on the central shaft; further: the turning power input mechanism A and the turning transmission mechanism B which are coaxially arranged have a relative rotating angle range in a circumferential direction; the turning power input mechanism A sequentially rotates in an angle I, an angle range II and an angle III while rotating relative to the turning transmission mechanism B from one end angle to the other end angle of the relative rotating angle range; when the turning power input mechanism A is within the angle range IL, the cam lock driven by the compression spring is locked at the housing in meshing manner to lock the turning transmission mechanism B, so that the turning transmission mechanism B and linear power output mechanism D remain relatively stationary; when the turning power input mechanism A is at the angle I, the cam lock driven by the lifting ring separates from the housing to release the turning transmission mechanism B; in addition, the turning transmission mechanism B is able to rotate to a first circumferential direction away from the angle range II accompanied with the turning power input mechanism A, and drive the linear power output mechanism D to displace; when the turning power input mechanism A is at the angle III, the cam lock driven by the lifting ring separates from the housing to release the turning transmission mechanism B; in addition, the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction.

Preferably, an angle range between the angle I and the angle III defines the angle range II.

Preferably, a plurality of engagement locked positions are arranged at an opening of the housing along the circumferential direction; along with rotation of the cam lock, the housing is able to be meshed to a corresponding engagement locked position by the cam lock.

Preferably, a pin hole of the wrench matches with a fan-shaped hole of the central shaft via a pin; an angle of the fan-shaped hole forms the relative rotating angle range; the wrench extends downwards out of a boss; the lifting ring is provided with a wrench fitting groove; and the boss is engaged in the wrench fitting groove.

Preferably, when the pin is located at one end of the fan-shaped hole, the wrench is at the angle I; when the pin is located at the other end of the fan-shaped hole, the wrench is at the angle III; when the pin is located between one end and the other end of the fan-shaped hole, the wrench is within the angle range II.

Preferably, the lifting ring is provided with a drive ramp; the cam lock is provided with a driven ramp, and the driven ramp matches with the drive ramp; when the lifting ring driven by the wrench rotates within the angle range II, there is a relative rotation between the lifting ring and the cam lock; when the lifting ring driven by the wrench rotates to the angle I and the angle III, the driven ramp is driven by the drive ramp, so that the cam lock is away from the housing, to separate from an engagement locking with the housing.

Preferably, the wrench is provided with a cover plate; the cam lock is provided with a compression spring support surface; a compression spring is connected between the cover plate and the compression spring support surface.

Preferably, a limit boss is arranged at the opening of the housing; and an angle limiting groove matching with the limit boss is arranged on the wrench.

A surgical instrument with bending control mechanism according to the present invention comprises the above-mentioned bending control mechanism.

Preferably, the surgical instrument is a surgical stapler; the linear power output mechanism D of the bending control mechanism is connected to the jaw of the stapler.

Compared with the prior art, the present invention has the following beneficial effects:

1. By the present invention, one or more locations are able to be locked in the operation, so as to bend and fix the stapler jaw to the required position, to complete the operation.

2. The present invention is provided with simple mechanism and fewer parts; most of the parts are made by injection molding process, so they are simple to manufacture and with low cost.

3. The bending control mechanism according to the present invention is able to be widely applied to other mechanical operating parts; it is easy to control and switch over.

BRIEF DESCRIPTION OF THE DRAWINGS

Other features, objects, and advantages of the present invention will become more apparent from reading the description of non-limiting embodiments detailed with reference to the following figures.

Figure 1:
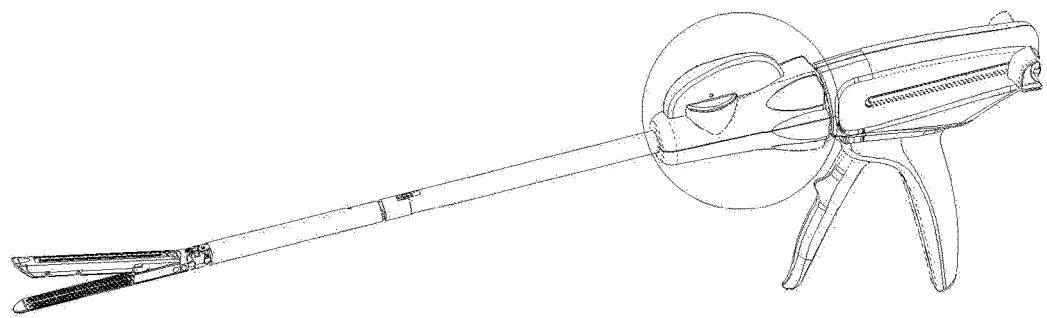
FIG. 1 is a main appearance diagram of a surgical stapler comprising bending control mechanism.

In the drawings:
1—wrench;
102—pin hole;
104—cover plate;
105—boss;
3—central shaft;
301—gear;
303—fan-shaped hole;
304—connecting groove;
5—rack;
501—rack structure;
6—pin;
7—housing;
701—opening;
702—locating tooth space;
8—lifting ring;
801—wrench fitting groove;
802—drive ramp;
9—cam lock;
901—connection boss;
902—locating tooth;
903—compression spring support surface;
904—driven ramp;
10—compression spring.

DETAILED DESCRIPTION OF THE PREFERRED EMBODIMENT

The invention is described in detail as follows with reference to specific embodiments. The following embodiments will help provide further understanding of the invention for those skilled in the art, and not in any way limit the invention. It shall be noted that several variants and improvements is able to be made without departing from concept of the invention for ordinary persons skilled in the art. All these fall within the protection scope of the invention.

The present invention provides a surgical instrument with a bending control mechanism, comprising the bending control mechanism. The surgical instrument is a surgical stapler; a linear power output mechanism D of the bending control mechanism is connected to a jaw of the stapler.

As shown in FIG. 1, the present invention provides an endoscopic surgical stapler with the bending control mechanism. The endoscopic surgical stapler comprises a tubular structure; the tubular structure is provided with a stapler jaw at a remote end, and a near end is connected to the bending control mechanism.

Figure 2:
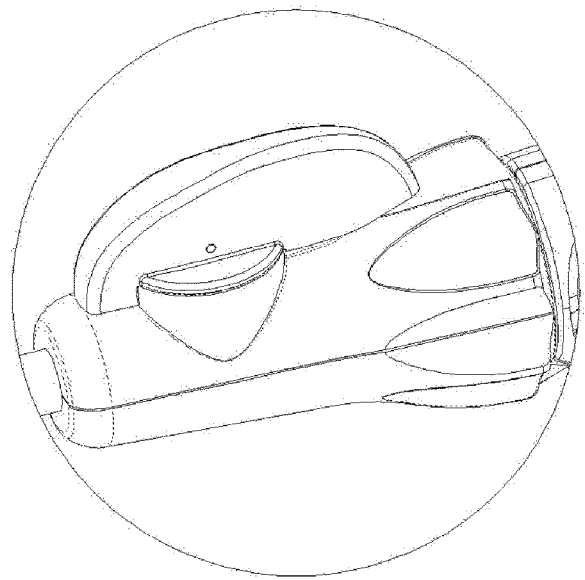
FIG. 2 is a main appearance diagram of the bending control mechanism.

FIG. 2 shows the bending control mechanism in the present invention; the bending control mechanism comprises a wrench 1 and a housing 7, wherein the wrench 1 is installed on the housing 7.

Specifically, the bending control mechanism comprises a wrench constituting a turning power input mechanism A and a lifting ring which synchronously rotates with the wrench; a central shaft 3 constituting a turning transmission mechanism B; a cam lock 9, a compression spring 10 and a housing 7 constituting a locking mechanism C, wherein the cam lock 9 is engaged with the turning transmission mechanism B; and a rack 5 constituting a linear power output mechanism D, wherein the rack 5 is engaged with a gear 301 arranged on the central shaft 3; further: the turning power input mechanism A and the turning transmission mechanism B which are coaxially arranged have a relative rotating angle range in a circumferential direction; the turning power input mechanism A sequentially rotates in an angle I, an angle range II and an angle III while rotating relative to the turning transmission mechanism B from one end angle to the other end angle of the relative rotating angle range; when the turning power input mechanism A is within the angle range II, the cam lock 9 driven by the compression spring 10 is locked at the housing in meshing manner to lock the turning transmission mechanism B, so that the turning transmission mechanism B and linear power output mechanism D remain relatively stationary; when the turning power input mechanism A is at the angle I, the cam lock 9 driven by the lifting ring 8 separates from the housing to release the turning transmission mechanism B; in addition, the turning transmission mechanism B is able to rotate to a first circumferential direction away from the angle range II accompanied with the turning power input mechanism A, and drive the linear power output mechanism D to displace; when the turning power input mechanism A is at the angle III, the cam lock 9 driven by the lifting ring 8 separates from the housing to release the turning transmission mechanism B; in addition, the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction.

Figure 3:
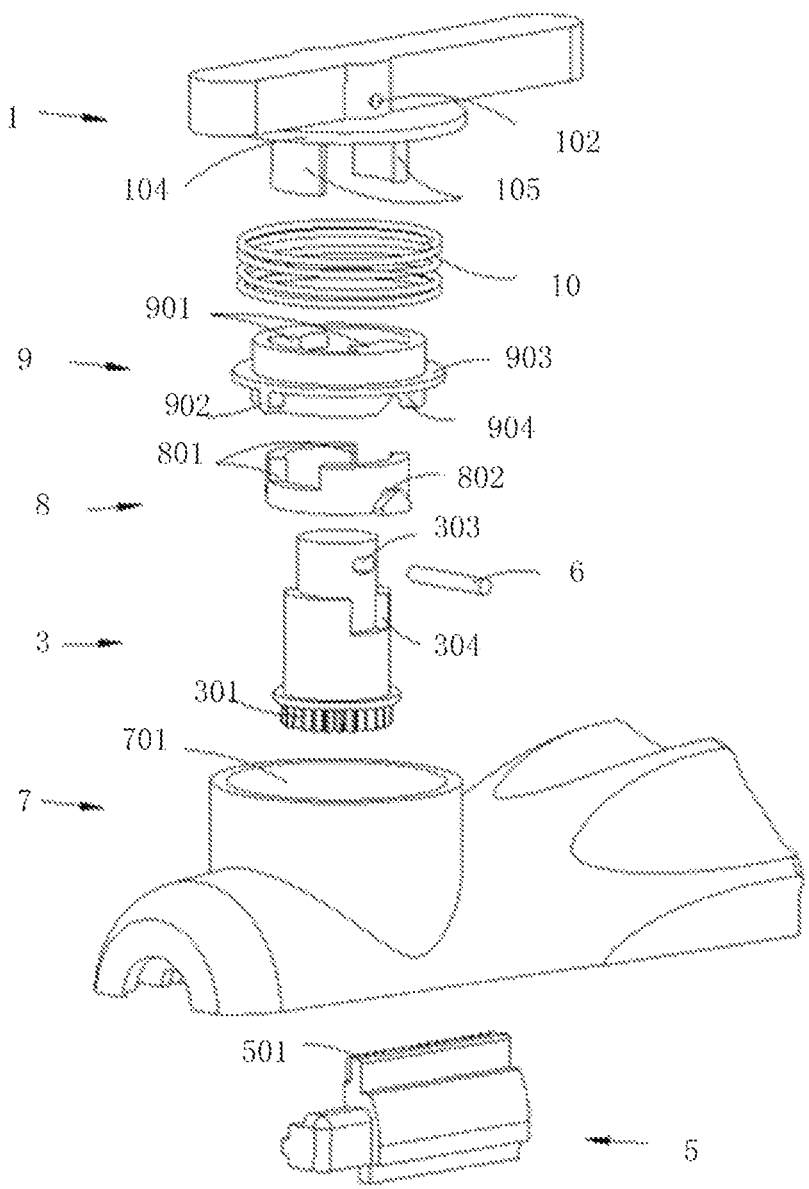
FIG. 3 is a detailed view of a split structure of the bending control mechanism.

FIG. 3 shows a bending control mechanism provided by the first embodiment of the present invention, comprising a wrench 1, a central shaft 3, a lifting ring 8, a cam lock 9, a housing 7 and a compression spring 10; wherein an opening 701 provided with a series of locating grooves 702 is arranged on the housing 7; the central shaft 3 is provided with a gear 301, which is connected with a stapler jaw by connecting with the rack 5 and further through a connecting device placed in the tubular structure; a lifting ring 8 in coaxial arrangement with the central shaft 3 has a drive ramp 802; a cam lock 9 in coaxial arrangement with the central shaft 3 comprises a connecting boss 901 connected with the central shaft 3, a driven ramp 904 matches with the drive ramp 802 of the lifting ring 8, and a locating tooth 902; the wrench 1 matches with the lifting ring 8 via a boss 105, and connected with the central shaft 3 via a pin 6; a compression spring 10 is arranged between the wrench 1 and the lifting ring 8.

Preferably, an angle range between the angle I and the angle III defines the angle range II.

Preferably, a plurality of engagement locked positions are arranged at the opening of the housing along the circumferential direction; along with rotation of the cam lock 9, the housing is able to be meshed to a corresponding engagement locked position by the cam lock 9.

More specifically, the surgical instrument is a surgical stapler; the linear power output mechanism D of the bending control mechanism is connected to the jaw of the stapler. Wherein, the locating groove 702 on the housing has a middle position, so that the stapler jaw is in a straight line state.

Preferably, a pin hole 102 of the wrench 1 matches with a fan-shaped hole 303 of the central shaft 3 via the pin 6; an angle of the fan-shaped hole 303 forms the relative rotating angle range; the wrench 1 extends downwards out of the boss 105; the lifting ring 8 is provided with a wrench fitting groove 801; and the boss 105 is engaged in the wrench fitting groove 801.

Preferably, when the pin 6 is located at one end of the fan-shaped hole 303, the wrench 1 is at the angle I; when the pin 6 is located at the other end of the fan-shaped hole 303, the wrench 1 is at the angle III; when the pin 6 is located between one end and the other end of the fan-shaped hole 303, the wrench 1 is within the angle range II.

Preferably, the lifting ring 8 is provided with a drive ramp 802; the cam lock 9 is provided with a driven ramp 904, and the driven ramp 904 matches with the drive ramp 802; when the lifting ring 8 driven by the wrench 1 rotates within the angle range II, there is a relative rotation between the lifting ring 8 and the cam lock 9; when the lifting ring 8 driven by the wrench 1 rotates to the angle I and the angle III, the driven ramp 904 is driven by the drive ramp 802, so that the cam lock 9 is away from the housing, to separate from an engagement locking with the housing.

Preferably, the wrench 1 is provided with a cover plate 104; the cam lock 9 is provided with a compression spring support surface 903; a compression spring 10 is connected between the cover plate 104 and the compression spring support surface 903.

Preferably, a limit boss is arranged at the opening of the housing; and an angle limiting groove matching with the limit boss is arranged on the wrench 1.

Figure 4:
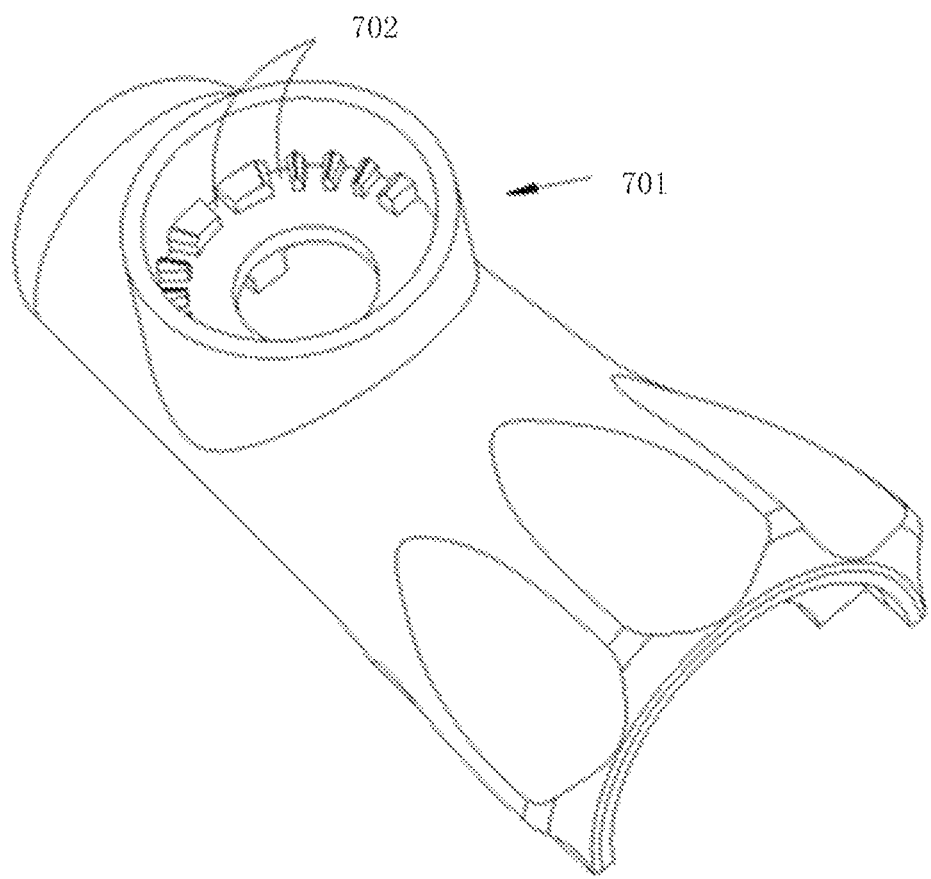
FIG. 4 is a top view of a housing of the bending control mechanism.

As shown in FIG. 4, the locating grooves 702 on the housing are circumferentially arrayed; a angle distribution of each locating groove 702 is not equidistant. In addition, a limit boss is arranged at the opening of the housing, to ensure that the wrench rotates in a certain angle, to prevent over-rotation.

As a variant embodiment of the first embodiment provided by the present invention, the angle distribution of the above-mentioned locking grooves is also able to be equal.

More specifically, the present invention is a bending control mechanism of endoscopic stapler, comprising a wrench 1, a compression spring 10, a cam lock 9, a lifting ring 8, a central shaft 3, a housing 7, a rack 5 and a pin 6. Wherein, the housing 7 has an opening, which is adapted for accommodating the wrench 1, the compression spring 10, the cam lock 9, the lifting ring 8 and the central shaft 3; the above-mentioned wrench 1, compression spring 10, cam lock 9, lifting ring 8 and central shaft 3 and the opening of the housing are arranged coaxially; a series of locating grooves 702 are arranged in the opening. The central shaft 3, the lifting ring 8 and the cam lock 9 are arranged from inside to outside; a connecting boss 901 of the cam lock 9 matches with a connecting groove 304 of the central shaft 3; a driven ramp 904 matches with a drive ramp 802 of the lifting ring 8; a locating tooth 902 is arranged in a series of locating grooves 702 on the housing. A boss 105 of the wrench 1 matches with a wrench fitting groove 801 of the lifting ring 8. The compression spring 10 is placed between a compression spring support surface 903 of the cam lock 9 and a cover plate 104 of the wrench 1. A pin hole 102 of the wrench 1 matches with a fan-shaped hole 303 of the central shaft 3 via the pin 6. The rack 5 is arranged in the housing 7, and engaged with a gear 301 of the central shaft 3.

When the wrench is rotated, the boss 105 of the wrench 1 drives the lifting ring 8 to rotate for an angle; the lifting ring 8 drives the driven ramp 904 of the cam lock 9 through the drive ramp 802, so that the cam lock 9 rises, and the locating tooth 902 and the locating groove 702 of the housing 7 disengage from an engaging state; when the wrench is rotated continuously, the pin 6 drives the central shaft 3 to rotate through the fan-shaped hole 303, and the central shaft 3 drives the cam lock 9 to rotate and drives the rack 5 to move forward and backward, to play a role of turning.

When the wrench 1 rotates to a next position, the wrench 1 will be released; the compression spring 10 will push the cam lock 9, to clamp the locating tooth 902 into another locating groove 702 of the housing 7. At this time, the cam lock 9 is able to lock the central shaft 3, for avoiding rotating freely. Since the locating tooth 902 of the cam lock 9 is engaged with a straight line segment of the locking groove 702 of the housing 7, a rotation of the gear 301 driven by the rack 5 is unable to rotate the cam lock 9 to achieve a purpose of locking.

A limit boss is arranged at the opening of the housing, to limit the rotation angle of the wrench and avoid excessive rotation.

Specific embodiments of the invention are described above. It shall be understood that the invention is not limited to the above-mentioned specific embodiments, and those skilled in the art is able to make different variants and modifications within the scope of the claims, and it shall not affect the substance of the invention.

What is claimed is:
1. A bending control mechanism, comprising:
   a wrench (1) constituting a turning power input mechanism A and a lifting ring (8) which synchronously rotates with the wrench (1);

a central shaft (3) constituting a turning transmission mechanism B;
a cam lock (9), a compression spring (10) and a housing (7) constituting a locking mechanism C, wherein the cam lock (9) is engaged with the turning transmission mechanism B;
a rack (5) constituting a linear power output mechanism D, wherein the rack (5) is engaged with a gear (301) arranged on the central shaft (3);
wherein:
the turning power input mechanism A and the turning transmission mechanism B which are coaxially arranged have a relative rotating angle range in a circumferential direction; the turning power input mechanism A sequentially rotates in an angle I, an angle range II and an angle III while rotating relative to the turning transmission mechanism B from one end angle to the other end angle of the relative rotating angle range;
when the turning power input mechanism A is within the angle range II, the cam lock (9) driven by the compression spring (10) is locked at the housing (7) in meshing manner to lock the turning transmission mechanism B, so that the turning transmission mechanism B and linear power output mechanism D remain relatively stationary;
when the turning power input mechanism A is at the angle I, the cam lock (9) driven by the lifting ring (8) separates from the housing (7) to release the turning transmission mechanism B; in addition, the turning transmission mechanism B is able to rotate to a first circumferential direction away from the angle range II accompanied with the turning power input mechanism A, and drive the linear power output mechanism D to displace;
when the turning power input mechanism A is at the angle III, the cam lock (9) driven by the lifting ring (8) separates from the housing (7) to release the turning transmission mechanism B; in addition, the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction;
a pin hole (102) of the wrench (1) matches with a fan-shaped hole (303) of the central shaft (3) via a pin (6); an angle of the fan-shaped hole (303) forms the relative rotating angle range;
the wrench (1) extends downwardly and outside a boss (105); the lifting ring (8) is provided with a wrench fitting groove (801); and the boss (105) is engaged in the wrench fitting groove (801).

2. The bending control mechanism according to claim 1, wherein an angle range between the angle I and the angle III defines the angle range II.

3. The bending control mechanism according to claim 2, wherein a plurality of engagement locked positions are arranged at an opening of the housing (7) along the circumferential direction; along with rotation of the cam lock (9), the housing (7) is able to be meshed to a corresponding engagement locked position by the cam lock (9).

4. The bending control mechanism according to claim 3, wherein a limit boss is arranged at the opening of the housing (7); and an angle limiting groove matching with the limit boss is arranged on the wrench (1).

5. The bending control mechanism according to claim 1, wherein when the pin (6) is located at one end of the fan-shaped hole (303), the wrench (1) is at the angle I; when the pin (6) is located at the other end of the fan-shaped hole (303), the wrench (1) is at the angle III; when the pin (6) is located between one end and the other end of the fan-shaped hole (303), the wrench (1) is within the angle range II.

6. The bending control mechanism according to claim 5, wherein the wrench (1) is provided with a cover plate (104); the cam lock (9) is provided with a compression spring support surface (903); the compression spring (10) is connected between the cover plate (104) and the compression spring support surface (903).

7. The bending control mechanism according to claim 1, wherein the lifting ring (8) is provided with a drive ramp (802); the cam lock (9) is provided with a driven ramp (904), and the driven ramp (904) matches with the drive ramp (802);
when the lifting ring (8) driven by the wrench (1) rotates within the angle range II, there is a relative rotation between the lifting ring (8) and the cam lock (9);
when the lifting ring (8) driven by the wrench (1) rotates to the angle I and the angle III, the driven ramp (904) is driven by the drive ramp (802), so that the cam lock (9) is away from the housing (7), to separate from an engagement locking with the housing (7).

8. A surgical instrument with a bending control mechanism, comprising the bending control mechanism which comprises:
a wrench (1) constituting a turning power input mechanism A and a lifting ring (8) which synchronously rotates with the wrench (1);
a central shaft (3) constituting a turning transmission mechanism B;
a cam lock (9), a compression spring (10) and housing (7) constituting a locking mechanism C, wherein the cam lock (9) is engaged with the turning transmission mechanism B;
a rack (5) constituting a linear power output mechanism D, wherein the rack (5) is engaged with a gear (301) arranged on the central shaft (3);
wherein:
the turning power input mechanism A and the turning transmission mechanism B which are coaxially arranged have a relative rotating angle range in a circumferential direction; the turning power input mechanism A sequentially rotates in an angle I, an angle range II and an angle III while rotating relative to the turning transmission mechanism B from one end angle to the other end angle of the relative rotating angle range;
when the turning power input mechanism A is within the angle range II, the cam lock (9) driven by the compression spring (10) is locked at the housing (7) in meshing manner to lock the turning transmission mechanism B, so that the turning transmission mechanism B and linear power output mechanism D remain relatively stationary;
when the turning power input mechanism A is at the angle I, the cam lock (9) driven by the lifting ring (8) separates from the housing (7) to release the turning transmission mechanism B; in addition, the turning transmission mechanism B is able to rotate to a first circumferential direction away from the angle range II accompanied with the turning power input mechanism A, and drive the linear power output mechanism D to displace;

when the turning power input mechanism A is at the angle III, the cam lock (9) driven by the lifting ring (8) separates from the housing (7) to release the turning transmission mechanism B; in addition, the turning transmission mechanism B is able to rotate to a second circumferential direction away from the angle range II accompanied with the turning power input mechanism A, and drive the linear power output mechanism D to displace; wherein the first circumferential direction is opposite to the second circumferential direction;

a pin hole (102) of the wrench (1) matches with a fan-shaped hole (303) of the central shaft (3) via a pin (6); an angle of the fan-shaped hole (303) forms the relative rotating angle range;

the wrench (1) extends downwardly and outside a boss (105); the lifting ring (8) is provided with a wrench fitting groove (801); and the boss (105) is engaged in the wrench fitting groove (801).

9. The bending control mechanism according to claim 8, wherein an angle range between the angle I and the angle III defines the angle range II.

10. The bending control mechanism according to claim 9, wherein a plurality of engagement locked positions are arranged at an opening of the housing (7) along the circumferential direction; along with rotation of the cam lock (9), the housing (7) is able to be meshed to a corresponding engagement locked position by the cam lock (9).

11. The bending control mechanism according to claim 10, wherein a limit boss is arranged at the opening of the housing (7); and an angle limiting groove matching with the limit boss is arranged on the wrench (1).

12. The surgical instrument according to claim 10, wherein the surgical instrument is a surgical stapler; the linear power output mechanism D of the bending control mechanism is connected to jaw of the stapler.

13. The bending control mechanism according to claim 8, wherein when the pin (6) is located at one end of the fan-shaped hole (303), the wrench (1) is at the angle I; when the pin (6) is located at the other end of the fan-shaped hole (303), the wrench (1) is at the angle III; when the pin (6) is located between one end and the other end of the fan-shaped hole (303), the wrench (1) is within the angle range II.

14. The bending control mechanism according to claim 13, wherein the wrench (1) is provided with a cover plate (104); the cam lock (9) is provided with a compression spring support surface (903); the compression spring (10) is connected between the cover plate (104) and the compression spring support surface (903).

15. The surgical instrument according to claim 14, wherein the surgical instrument is a surgical stapler; the linear power output mechanism D of the bending control mechanism is connected to jaw of the stapler.

16. The bending control mechanism according to claim 8, wherein the lifting ring (8) is provided with a drive ramp (802); the cam lock (9) is provided with a driven ramp (904), and the driven ramp (904) matches with the drive ramp (802);

when the lifting ring (8) driven by the wrench (1) rotates within the angle range II, there is a relative rotation between the lifting ring (8) and the cam lock (9);

when the lifting ring (8) driven by the wrench (1) rotates to the angle I and the angle III, the driven ramp (904) is driven by the drive ramp (802), so that the cam lock (9) is away from the housing (7), to separate from an engagement locking with the housing (7).

17. The surgical instrument according to claim 16, wherein the surgical instrument is a surgical stapler; the linear power output mechanism D of the bending control mechanism is connected to a jaw of the stapler.

18. The surgical instrument according to claim 8, wherein the surgical instrument is a surgical stapler; the linear power output mechanism D of the bending control mechanism is connected to a jaw of the stapler.

* * * * *